United States Patent [19]
Biche

[11] Patent Number: 5,944,697
[45] Date of Patent: Aug. 31, 1999

[54] PERCUTANEOUS CATHETER INTRODUCER

[75] Inventor: Joseph E. Biche, Mayfield, N.Y.

[73] Assignee: Universal Medical Instrument Corp., Ballston Spa, N.Y.

[21] Appl. No.: 08/735,483

[22] Filed: Oct. 23, 1996

Related U.S. Application Data

[63] Continuation of application No. 08/251,738, May 31, 1994, abandoned.

[51] Int. Cl.⁶ ..................................................... A61M 5/32
[52] U.S. Cl. .......................... 604/174; 604/246; 604/256; 604/523
[58] Field of Search ..................... 604/158, 164, 604/174, 246, 264, 280, 283, 256, 523

[56] References Cited

U.S. PATENT DOCUMENTS

| | | |
|---|---|---|
| 4,360,024 | 11/1982 | Wallace . |
| 4,468,224 | 8/1984 | Enzmann et al. ........................ 604/247 |
| 4,568,336 | 2/1986 | Cooper . |
| 4,826,477 | 5/1989 | Adams . |
| 4,842,591 | 6/1989 | Luther . |
| 4,909,798 | 3/1990 | Fleischhacker . |
| 4,929,235 | 5/1990 | Merry . |
| 4,946,133 | 8/1990 | Johnson . |
| 4,960,412 | 10/1990 | Fink . |
| 5,114,408 | 5/1992 | Fleischhaker et al. .................. 604/167 |
| 5,125,903 | 6/1992 | McLaughlin . |
| 5,129,891 | 7/1992 | Young . |
| 5,137,519 | 8/1992 | Littrell et al. ........................... 604/174 |
| 5,176,652 | 1/1993 | Littrell . |
| 5,180,373 | 1/1993 | Green . |
| 5,207,656 | 5/1993 | Kranys . |
| 5,211,633 | 5/1993 | Stouder . |
| 5,242,431 | 9/1993 | Kristiansen . |
| 5,267,966 | 12/1993 | Paul . |
| 5,267,982 | 12/1993 | Sylvanowicz ............................ 604/280 |
| 5,273,545 | 12/1993 | Hunt . |
| 5,273,546 | 12/1993 | McLaughlin . |
| 5,279,571 | 1/1994 | Larkin . |
| 5,282,790 | 2/1994 | Clement . |
| 5,324,260 | 6/1994 | O'Neill et al. ............................ 604/96 |

*Primary Examiner*—Corrine McDermott
*Assistant Examiner*—Cris L. Rodriguez
*Attorney, Agent, or Firm*—Workman, Nydegger, Seeley

[57] ABSTRACT

A percutaneous catheter introducer (PCI) is disclosed having a transparent housing, a valve seal disposed within the housing, a rotatable suture ring including a tab, and a sheath extending through the suture ring and into the housing. The transparent housing allows for detection of emboli formation inside the percutaneous catheter introducer. The rotatable suture ring permits versatility of movement when sewing the PCI device to the patient.

7 Claims, 2 Drawing Sheets

PERCUTANEOUS CATHETER INTRODUCER

This application is a continuation of application Ser. No. 08/251,738, filed May 31, 1994, now abandoned.

FIELD OF THE INVENTION

The present invention relates generally to surgical implements for introducing devices into the human body. In particular, the present invention is concerned with percutaneous catheter introducers.

BACKGROUND OF THE INVENTION

Percutaneous catheter introducers (PCIs) are currently used with catheters for performing percutaneous transluminal angioplasty (PTA) as well as angiographic procedures, such as inserting x-ray contrast fluid into the coronary artery. The main functions of PCI devices are to provide a hemostasis valve seal to prevent leakage of blood upon insertion of a catheter into an artery, as well as introduction of fluids into the body through a side arm assembly.

One particular PCI device is disclosed in U.S. Pat. No. 5,114,408 to Fleischhaker et al. which includes a one-piece hemostasis seal valve which is formed of a longitudinally extending valve housing having a first opening and a central longitudinal passage communicating with an opposite second opening. A cap having a hole is provided to permit insertion of a catheter. Also provided is a one-piece seal having a conical opening and a concave exit face.

U.S. Pat. No. 5,273,546 discloses a hemostasis valve for a PCI. The hemostasis valve is disk-shaped and is fitted into a circular seat.

U.S. Pat. No. 5,176,652 to Littrell discloses a hemostasis valve. The hemostasis valve comprises a gasket including a pair of opposed sides with a first slit extending inwardly of the gasket member from one of the opposed sides. Both of the slits are of a shape defining a plurality of radii extending from a common origin.

U.S. Pat. No. 5,267,966 to Paul discloses a hemostasis cannula used in angiographic studies and method of making a valve for the same. The valve body includes an opening in one side thereof which forms a seal around a catheter enclosed within the cannula. The opening includes a cylindrical recess and four tapered slits extending from the base of the recess to a point shaped opening at the other end of the valve body. The slits are made with a four-sided pyramid shaped tool.

In addition to PCI devices, valves or seals are used in other types of medical devices. U.S. Pat. No. 5,282,790 discloses a cannula seal used in laparoscopic surgical procedures. In addition to a conventional seal, a duckbill flap valve is used for pneumatically sealing a channel. U.S. Pat. No. 5,273,545 discloses a seal for an endoscopic laparoscopic cannula. The seal has a tri-cuspid leaf valve. U.S. Pat. No. 5,211,633 to Stouder, Jr. discloses a selectable seal cannula to ensure a fluid-tight fit around laparoscopic medical devices.

U.S. Pat. No. 5,180,373 discloses using a housing formed of a suitable material such as polycarbonate, or polyethylene. One of the preferred materials is LEXAN®. U.S. Pat. No. 5,207,656 discloses that one of the materials used to form a foamed elastomeric partition or seal is KRATON®.

U.S. Pat. No. 5,129,891 discloses a connector for detachably securing an end of a tube, such as a catheter, to a fluid port of a fluid transfer assembly, such as an implantable device. The connector includes a sleeve which fits within the body part and defines an aperture for compressively receiving an end of the tube which has been fitted over a fluid port of the transfer assembly.

U.S. Pat. No. 5,242,431 discloses a suture sleeve assembly with slidable compression collar. The suture sleeve assembly is for gripping and anchoring the lead body of an implantable medical device, such as a cardiac pacemaker. Disposed about the tubular member is a collar movable longitudinally along the tubular member from a first, open position to a second position in which the collar compresses a portion of the tubular member into gripping engagement with the outer surface of the lead body.

U.S. Pat. No. 4,826,477 discloses a connector for blood handling systems. The connector includes a dual-acting coupler with a first coupling section for joining to the flexible conduit and a second coupling section, which can be of conventional design, for joining to the second component. The first coupling section includes an outer tapered portion which tapers inward to a rounded thin edge at the end of the coupler. The connector further includes a generally ring-shaped compression collar having an inner tapered portion for encircling the outer tapered portion of the coupler.

The above related art summaries are merely representative of portions of the inventions disclosed in each reference. In no instance should these summaries substitute for a thorough reading of each individual reference.

SUMMARY OF THE INVENTION

A difficulty of the aforementioned PCI devices is the inability to monitor the introduction of air into the PCI to detect emboli (blood clot) formation. The past PCI devices included a housing made from opaque material which did not allow for visual inspection. A feature of the PCI of the present invention is the advantage of being able to visually monitor emboli formation through a transparent LEXAN® housing and cap. The ability to monitor emboli formation is important in view of the inherent danger to the patient of the possibility stroke or other blockage caused by emboli traveling through the circulating system.

During assembly, a LEXAN® cap is snapped onto the LEXAN® main body. This snap fit is unique in view of the fact that LEXAN® is known to be a rigid material. Since LEXAN® is rigid, it would not be apparent that it would bend when the cap is snapped onto the main body.

Another feature of the present invention is that the seal is formed having a single sealant layer as opposed to a dual sealant layer having a dead space therebetween. The single layer reduces the amount of material necessary and the complexity of manufacture of the part. The absence of dead space helps prevent the formulation of emboli.

Another difficulty with past PCI devices is the inability to position the suture ring after the PCI has been inserted into the body. After the PCI device has been inserted into the body, a tab on the suture ring is used to sew the PCI to the patient's skin to prevent unwanted movement. In the present invention, a rotatable suture ring compensates for various angles of sewing of the PCI device onto the body. Another advantage of the suture ring is that it serves as a strain relief to prevent kinks and bends in the sheath where it is attached to the rigid body.

Another feature of the present invention is an improved connector used to attach the side arm assembly onto the main body. The side arm tubing is inserted over a nipple after which a ring is snapped over a barb on the nipple such that the ring cannot be removed without damage to the parts. This fitting provides an advantage in that the side arm assembly will not become disassembled during use.

These and other objects and advantages of the present invention will be better understood and become apparent when consideration is given to the following details and description when taken in conjunction with the annexed drawings.

DETAILED DESCRIPTION OF THE PREFERRED EMBODIMENTS

Figure 1:
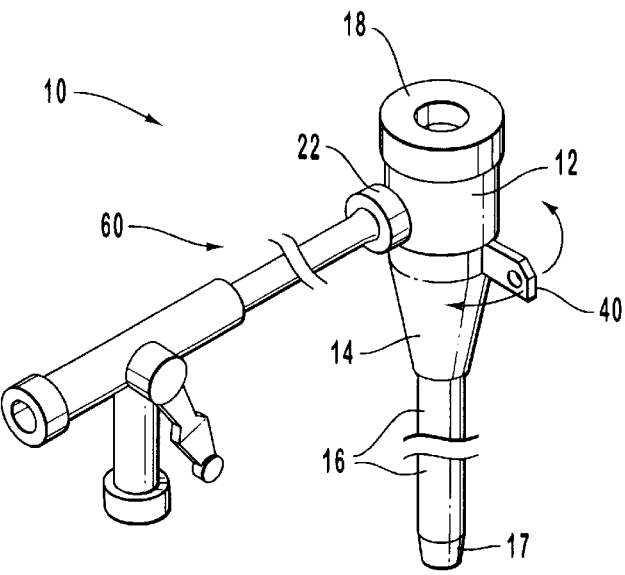
FIG. 1 is a perspective view of the percutaneous catheter introducer of the present invention.

Referring to FIG. 1, a Percutaneous Catheter Introducer (PCI) 10 is shown having a main body or housing 12, a rotatable suture ring 14, sheath 16 made of a fluorinated ethylene propylene (FEP) or other synthetic resin polymer, a cap 18, and a side arm assembly 60. Directional arrows show rotation of the tab 40 and suture ring 14. The rotation of the tab 40 and suture ring 14 permit positioning of the tab 40 prior to sewing the tab 40 to the patient.

The bottom of the sheath 16 includes a taper 17. The taper 17 is shaped by heat forming to produce an even transition to a dilator. The dilator (not shown) is a tube inserted through the sheath 16 to provide rigidity to the sheath and prevent the sheath 16 from bending in an accordian-like manner upon insertion of the PCI into the body. When the taper 17 is formed, the wall thickness and inside diameter of the sheath 16 are reduced such that an even transition is provided between the dilator and sheath 16 and the inside diameter of the sheath 16 matches the outside diameter of the dilator.

Figure 2:
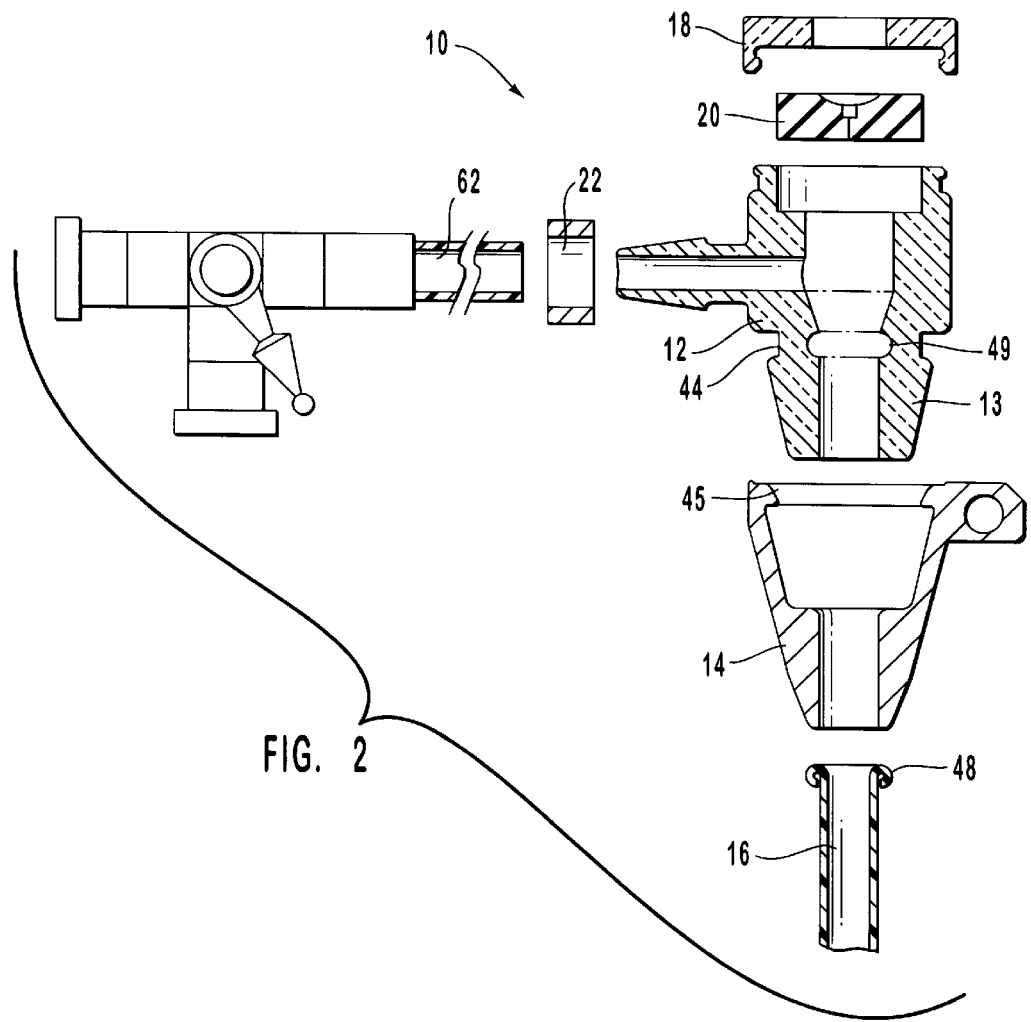
FIG. 2 is an exploded cutaway view of the percutaneous catheter introducer of the present invention.

FIG. 2 shows an exploded cutaway view of the PCI 10. The main body or housing 12 and cap 18 are formed of transparent material such as LEXAN® brand polycarbonate manufactured and marketed by General Electric Company, Pittsfield, Mass. The seal or gasket 20 may be formed from a material, such as molded liquid silicone rubber (LSR) which provides adequate sealing about a device, such as a catheter, guidewire, or obterator against the back flow of blood and in the absence of the device. The side arm assembly tubing 62 is made from a transparent polyvinyl chloride (PVC) tubing. The transparent tubing allows for visual monitoring of blood and other products, such as pharmaceuticals present or introduced into in the side arm assembly 60.

The suture ring 14 is made of a thermoplastic elastomer material such as KRATON® elastomer, a material sold by Shell Chemical Company. The sheath 16 is made of FEP or other synthetic resin polymer. The suture ring 14 serves as a stain relief for the sheath 16 to prevent the sheath 16 from kinks and unwanted bends during handling and when inserting the sheath into the body.

Figure 3:
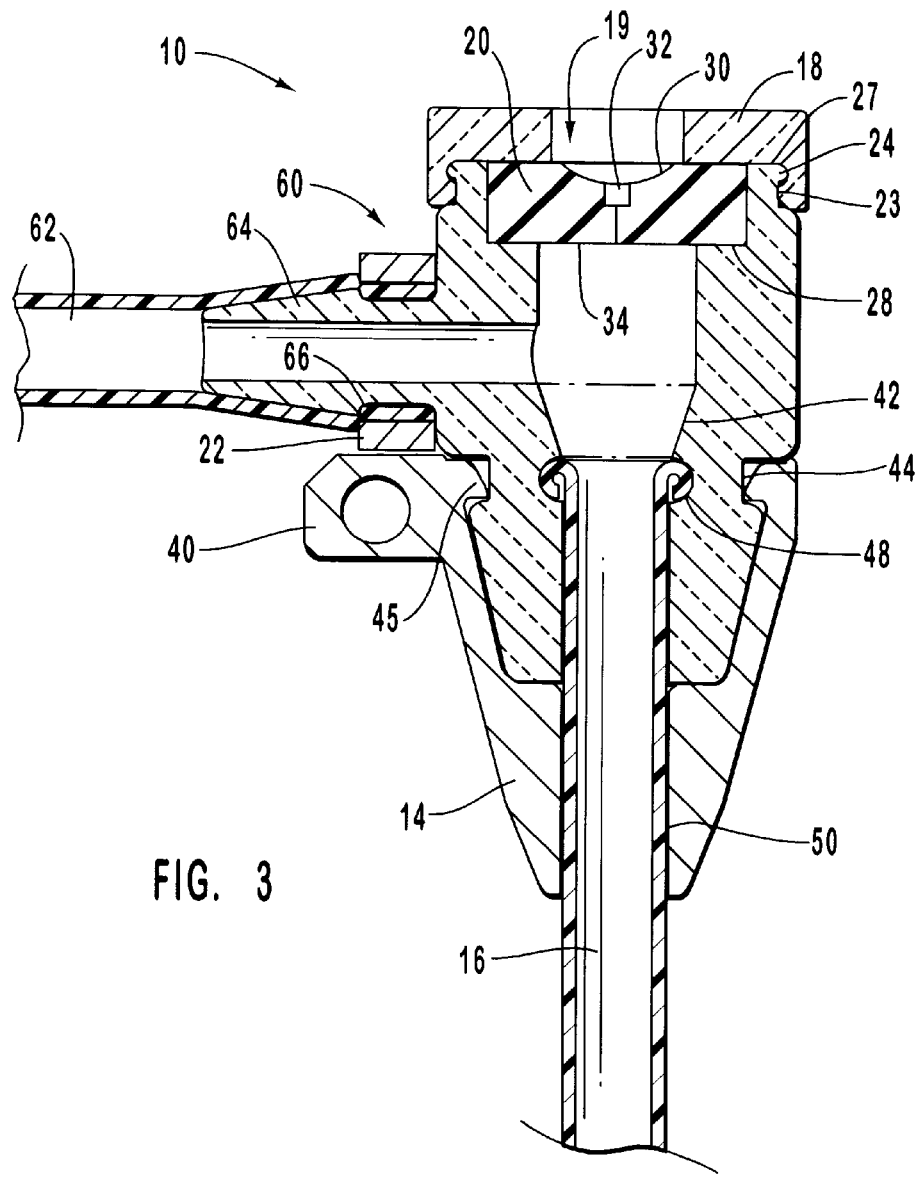
FIG. 3 is a cutaway side view of the percutaneous catheter introducer of present invention.

FIG. 3 shows the PCI 10 in assembled form. The sheath 16 is molded into the main body 12. In order to provide a tight grip, the end 48 of the sheath 16 is heat curled. The main body 12 has an inner taper 42 which allows for one of many French sizes of sheath 16 to be selected. The larger French sizes would be positioned at an identical position of taper 42, however the angle of the taper varies with French size.

The assembly of the sheath 16 into the main body 12 includes first, heat curling the end 48. After the end 48 is heat curled, a core pin is inserted into sheath 16 of a particular French size. The sheath 16 and core pin are inserted into a mold and the material for forming the main body 12 is injected about the core pin and sheath 16 such a that the heat curled portion 48 is formed into an annular cavity 49 of the main body 12.

The rotatable suture ring 14 is assembled over the main body 12 by slipping the annular ring 45 over the frustoconical portion 13 of the main body 12 and into an annular grooved surface 44. Each French size has color coded suture ring for quick identification by the user. After molding, sheath 16 becomes rigidly affixed to the main body 12. Thus, when the rotatable suture ring 14 is rotated, it moves about both the sheath 16 and frustoconical portion 13. The side arm assembly 60 is positioned such that the tab 40 includes a clearance underneath the ring 22.

The seal or gasket 20 includes a flat lower surface 34 and a concave entry face 30 which converges into a pilot opening 32. The lower surface may also be covex between the ledge surfaces 28. The seal 20 is inserted into the main body 12 such that it rests on ledge surfaces 28. A cap 18, having an annular hole 19 for insertion of a device, is inserted over the seal 20 and snapped into place to lock the seal 20 in position. The cap 18 includes an annular snap connector 23 which mates with an annular snap connector 24 on the main body 12. Silicone or other lubricant is placed into the entry face 30 for ease of insertion of a dilator or other device.

Figure 4:
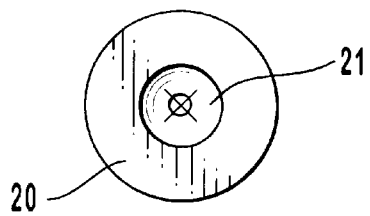
FIG. 4 is a plan view of the seal valve of the percutaneous catheter introducer of the present invention.

FIG. 4 shows a plan view of the seal 20 having an X-cut 21 therein. A Y-cut or slit may also be used.

The side arm assembly 60 is mounted by placing a ring 22 on the side arm tubing 62. The side arm tubing 62 is then slid over a tapered nipple coupler 64. The ring 20 is then slid over the tubing 62 and nipple coupler 64 until it is engaged on the other side of barb 66. The barb 66 does not allow the ring 22 to be removed absent destruction of either the tubing 62, ring 22, or nipple coupler 64.

The embodiments disclosed herein have been discussed for the purpose of familiarizing the reader with the novel aspects of the invention. Although preferred embodiments of the invention have been shown, many changes, modifications and substitutions may be made by one having ordinary skill in the art without necessarily departing from the spirit and scope of the invention as described in the following claims.

I claim:

1. Percutaneous catheter introducer comprising:
    a housing;
    a valve seal disposed within said housing;
    a suture ring including a tab, rotationally attached to said housing; and
    a sheath extending through said suture ring into said housing, wherein said suture ring extends over an end of said housing and is slidably attached to a portion of said sheath, and said suture ring is formed from an elastomeric material to thereby provide strain relief to prevent the sheath from forming kinks and unwanted bends during handling and when inserting the sheath into the body.

2. The percutaneous catheter introducer of claim 1, wherein the sheath affixed in said housing comprises an end that is heat curled.

3. The percutaneous catheter introducer of claim 2, wherein said housing comprises an inner periphery that includes a tapered portion, and wherein said end of the sheath affixed to the housing is attached at the tapered portion of the inner periphery of the housing.

4. The percutaneous catheter introducer of claim 1, further comprising a side arm assembly, and wherein said tab on the suture ring is positioned such that it clears the side are assemble upon rotation.

5. The percutaneous catheter of claim 1, wherein the housing includes a grooved surface and the suture ring includes a guide surface frictionally engaged with said grooved surface, whereby the groove surface does not freely slide along said guide surface.

6. The percutaneous catheter introducer of claim 1, wherein said tab of the suture ring further comprises a hole therein for holding a suture.

7. The percutaneous catheter claims 1, wherein the housing is transparent.

* * * * *

UNITED STATES PATENT AND TRADEMARK OFFICE
CERTIFICATE OF CORRECTION

PATENT NO.    : 5,944,697
DATED         : August 31, 1999
INVENTOR(S)   : Joseph E. Biche It is certified that error appears in the above-identified patent and that said Letters Patent is hereby corrected as shown below:

Column 1,
Line 20, after "as well as" change "introduction of" to -- to introduce --

Column 3,
Line 57, before "relief" change "stain" to -- strain --

Column 5,
Lines 5-6, after "side" change "are assemble" to -- arm assembly --

Column 6,
Line 6, after "catheter" change "claims" to -- of claim --

Signed and Sealed this

Sixteenth Day of October, 2001

Attest:

NICHOLAS P. GODICI
*Acting Director of the United States Patent and Trademark Office*

*Attesting Officer*